(12) United States Patent
Kreuzer et al.

(10) Patent No.: US 12,171,561 B2
(45) Date of Patent: Dec. 24, 2024

(54) CUFF WITH INTEGRATED SIGNAL RECORDER FOR LONG-TERM MEASUREMENTS OF BIOSIGNALS FROM A LIVING BODY

(71) Applicant: Berne University of Applied Sciences, Biel (CH)

(72) Inventors: Samuel Kreuzer, Koniz (CH); Tobias Bertos, Biberist (CH); Thomas Niederhauser, Oberwangen b. Bern (CH)

(73) Assignee: Berne University of Applied Sciences, Biel (CH)

( * ) Notice: Subject to any disclaimer, the term of this patent is extended or adjusted under 35 U.S.C. 154(b) by 128 days.

(21) Appl. No.: 17/255,266

(22) PCT Filed: Jun. 24, 2019

(86) PCT No.: PCT/EP2019/066693
§ 371 (c)(1),
(2) Date: Dec. 22, 2020

(87) PCT Pub. No.: WO2020/002250
PCT Pub. Date: Jan. 2, 2020

(65) Prior Publication Data
US 2021/0121116 A1 Apr. 29, 2021

(30) Foreign Application Priority Data
Jun. 26, 2018 (EP) ..................................... 18179712

(51) Int. Cl.
*A61B 5/00* (2006.01)
*A61B 5/01* (2006.01)
(Continued)

(52) U.S. Cl.
CPC ............ *A61B 5/333* (2021.01); *A61B 5/0006* (2013.01); *A61B 5/01* (2013.01); *A61B 5/0531* (2013.01);
(Continued)

(58) Field of Classification Search
CPC ......... A61B 5/333; A61B 5/291; A61B 5/296; A61B 5/308; A61B 5/256; A61B 5/0006;
(Continued)

(56) References Cited

U.S. PATENT DOCUMENTS

2009/0171274 A1* 7/2009 Harlev ................. A61B 5/6859
604/95.04
2010/0185077 A1* 7/2010 Chang ..................... A61B 5/25
205/210
(Continued)

FOREIGN PATENT DOCUMENTS

CN 103190899 7/2013
CN 206355043 7/2017
(Continued)

*Primary Examiner* — Sana Sahand
(74) *Attorney, Agent, or Firm* — Defillo & associates, Inc.; Evelyn A. Defillo (57) ABSTRACT

A wearable cuff based on a carrier material with an integrated signal recorder for measurements of biosignals on the skin of a living body recording at an upper arm of a human body. At least one electrode is connected to the carrier material via a reversibly compressible material. The electrodes, the base of the main circuit, and the conductors of the signal recorder are based on one and the same flexible printed circuit board (FPCB). The carrier material is an elastic material. The conductors exhibit a zig-zag, U-shape, Ω-shape and/or a meandering form. The carrier material includes a woven and/or a nonwoven layer being coated with a thermoplastic polymer layer. A process to make the cuff, a process to measure biosignals on the skin of a living
(Continued)

body, for long-term ECG recording at an upper arm of a human body, and the use of the cuff to record biosignals on the skin of a living body.

18 Claims, 5 Drawing Sheets

(51) Int. Cl.
| | |
|---|---|
| *A61B 5/0531* | (2021.01) |
| *A61B 5/256* | (2021.01) |
| *A61B 5/268* | (2021.01) |
| *A61B 5/27* | (2021.01) |
| *A61B 5/282* | (2021.01) |
| *A61B 5/291* | (2021.01) |
| *A61B 5/296* | (2021.01) |
| *A61B 5/308* | (2021.01) |
| *A61B 5/333* | (2021.01) |

(52) U.S. Cl.
CPC ............. *A61B 5/256* (2021.01); *A61B 5/268* (2021.01); *A61B 5/27* (2021.01); *A61B 5/282* (2021.01); *A61B 5/291* (2021.01); *A61B 5/296* (2021.01); *A61B 5/308* (2021.01); *A61B 5/6824* (2013.01); *A61B 2560/0214* (2013.01); *A61B 2562/164* (2013.01)

(58) Field of Classification Search
CPC ......... A61B 5/01; A61B 5/0531; A61B 5/268; A61B 5/282; A61B 5/27; A61B 5/6824
See application file for complete search history.

(56) References Cited

U.S. PATENT DOCUMENTS

| | | | |
|---|---|---|---|
| 2014/0275931 A1 | 9/2014 | Kato | |
| 2015/0223716 A1 | 8/2015 | Korkala | |
| 2015/0313542 A1* | 11/2015 | Goldberg | G04B 47/063 |
| | | | 368/282 |
| 2016/0073886 A1* | 3/2016 | Connor | A61B 5/6887 |
| | | | 600/475 |
| 2016/0113544 A1* | 4/2016 | Li | A61B 5/25 |
| | | | 600/391 |
| 2017/0281038 A1 | 10/2017 | Cao | |
| 2018/0249767 A1* | 9/2018 | Begriche | A61B 5/25 |

FOREIGN PATENT DOCUMENTS

| | | |
|---|---|---|
| EP | 225156 | 6/1987 |
| EP | 1649805 | 4/2006 |
| EP | 3292885 | 3/2018 |
| WO | WO2010088325 | 8/2010 |
| WO | WO2010105053 | 9/2010 |
| WO | WO2017033058 | 3/2017 |

* cited by examiner

CUFF WITH INTEGRATED SIGNAL RECORDER FOR LONG-TERM MEASUREMENTS OF BIOSIGNALS FROM A LIVING BODY

CROSS REFERENCE TO RELATED APPLICATION

This application is a national stage entry of PCT/EP2019/066693 filed Jun. 24, 2019, under the International Convention claiming priority over European Patent Application No. 18179712.7 filed Jun. 26, 2018.

FIELD OF THE INVENTION

The present invention relates to a robust, adaptive and easy wearable cuff with an integrated signal recorder for measurements of biosignals on the skin of a living body, in particular for long-term ECG recording at an upper arm of a human body, a process to make the cuff, a process to measure biosignals with the cuff, and to the use of the cuff.

BACKGROUND OF THE INVENTION

Cardiovascular diseases (CVD), such as cerebrovascular stroke, myocardial infarction or heart rhythm disorders, i.e. cardiac arrhythmias, are widely spread diseases in western countries. A highly established method to detect rare and short arrhythmias such as paroxysmal atrial fibrillation is the long-term electrocardiogram (ECG), with usual recording durations of 24 to 48 hours. For indicated patients, e.g. suffering a cryptogenic stroke where the etiology is unknown, repetitive or event-triggered ECG monitoring up to 30 days may be performed. In such cases, the prolonged ECG recording shows a higher detection rate and improved diagnostic outcome.

The today's state of the art technology for clinical long-term ECG monitoring are so called Holter monitors, which use pre-gelled (wet) skin electrodes. However, Holter monitors exhibit electrode-related limitations during prolonged application, such as drying out of the conductive gel, and adhesive altering. All these characteristics lower the signal quality over time. Further system-related drawbacks of said monitors are electrode and cable-motion artifacts as well as reduced patient comfort due to frequent skin irritations. As a conclusion thereof, the patient's compliance to such long-term ECG monitoring is often reduced.

To overcome the shortcomings of prolonged ECG recording with Holter monitors, tiny patch-type recorders have recently been suggested. However, such devices most typically are based on wet, i.e. pre-gelled, electrodes too and they use adhesives to fix said patch-type recorders to the skin, which may lead to skin irritations. In addition, such single-use recorders have a multilayer design having various components integrated, which results in complex manufacturing processes as compared to passive wet or dry electrodes.

Therefore, there is a need for a device to measure long-term ECG which overcomes the disadvantages of the present technologies. The device must enable long-term ECG recording with a high data quality at any time of the recording time. Hence, within the time span of measuring the ECG, there shall be no deterioration of the electrodes and the device must—when worn—not be vulnerable to get damaged, even when the patient is physically active. Additionally, the device shall be worn without the use of an adhesive to adhere the electrodes to the skin, to avoid potential skin irritations, and the wearing of the device shall provide no or only a slight reduction of patient comfort. It must be also possible to wear the device by individuals on places of the body with strong contractions and relaxations of the muscles under the device. Hence, the device must e.g. be also wearable at an upper arm of a human body.

SUMMARY OF THE INVENTION

Surprisingly, it was found that these requirements can be fulfilled with a robust, adaptive and easy wearable cuff (1) with an integrated signal recorder (2) for measurements of biosignals on the skin of a living body, in particular for long-term ECG recording at an upper arm (3) of a human body, wherein the cuff (1) is based on a carrier material (4) and the signal recorder (2) is comprising an optional ground electrode (21), one or more signal electrodes (22), a main circuit (23) comprising a base (23a), conductors (24) which connect the electrodes (21, 22) to each other and/or to the base (23a) of the main circuit (23), wherein at least one electrode (21, 22) is connected to the carrier material (4) via a reversibly compressible material (6), wherein:

- the electrodes (21, 22), the base (23a) of the main circuit (23) and the conductors (24) are based on one and the same flexible printed circuit board (FPCB) (5) and thus they exhibit no interfaces in between,
- the carrier material (4) is an elastic carrier material (4) having an elongation of at least 10%, in particular of at least 50%, at a tensile force of 1 N, when measured at 23° C. and 50% relative humidity, measured according to ISO 13934-1:2013, and wherein the conductors (24) exhibit a zig-zag, U-shape, Ω-shape and/or a meandering form, and/or
- the carrier material (4) is comprising a woven and/or a nonwoven layer (41) being coated with a thermoplastic polymer layer (42), wherein the thermoplastic polymer layer (42) preferably comprises—in particular is based on—polyurethane (PU).

Claimed also is a process to make the cuff (1) according to the invention, wherein:

- the one or more signal electrodes (22), the base (23a) of the main circuit (23), the conductors (24) and the optional ground electrode (21) are made from the same flexible printed circuit board (FPCB) (5),
- the amplifier (23b), the controller (23c), the battery (23d) and the optional memory (23e) and/or the optional transmitter or transceiver (23f), the optional DC-restorer (23g) and/or the optional feedback circuit (23h) are connected to the base (23a) and thus to the main circuit (23), preferably by soldering, welding, bonding, and/or gluing,
- the conductors (24) and the base (23a) of the main circuit (23) are mounted to the carrier material (4),
- the reversibly compressible material (6) is affixed to at least one electrode (21, 22) and/or to the carrier material (4), wherein the compressible material (6) connects the electrode (21, 22) to the carrier material (4), and
- the side of the FBCB (5), which is opposite to the electrodes (21, 22), may be coated with an optional dielectric coating (58).

Furthermore, claimed is also a process to measure biosignals on the skin of a living body, in particular for long-term ECG recording at an upper arm (3) of a human body, with the cuff (1) according to the invention, wherein the cuff (1) with the integrated signal recorder (2) is placed at a living body, in particular at the upper arm (3) of a human body, optionally reduces the common voltage with the optional feedback circuit (23h), the biosignals are measured, preferably continuously, with the electrodes (21, 22), optionally amplified and/or filtered by the preamplifier or buffer (22a), and transmitted via the conductors (24) to the main circuit (23) of the signal recorder (2).

Additionally, also claimed is the use of the cuff (1) according to the invention to record biosignals on the skin of a living body.

DETAILED DESCRIPTION OF THE INVENTION

The cuff (1), the process to make the cuff (1), the process to measure biosignals on the skin of a living body and the use of the cuff (1) according to the invention comprise surprisingly many advantages.

The cuff (1) allows a straight-forward measurement of biosignals on the outer skin of a living body. Hence, the cuff (1) can be used to measure a wide range of biosignals on the skin of living bodies, i.e. it is not limited to human bodies. The cuff (1) may be worn at various positions such as—by humans—at an upper arm and/or at the torso. The fact, that ECG-measurements can be performed at a high quality at an upper arm of a human is a big surprise and could not be expected.

Surprisingly, the cuff (1) provides a high comfort when worn. No external cables are required and the fixation of the cuff (1) is easy, in particular when the cuff (1) possesses elastic properties. Hence, the cuff (1) may be undressed and dressed by the patient himself, e.g. when taking a shower.

The electrodes (21, 22) have due to the reversibly compressible material (6) always a good contact to skin, even when the shape of the skin is changing e.g. due to muscle tension and relaxation.

When the cuff (1) is based on an elastic, i.e. flexible, carrier material (4), the cuff (1) can be also easily worn over days at parts of the body with changing dimensions, e.g. due to muscle motions. And thus, when worn properly, the cuff (1) provides about constant pressure by the carrier material (4) to the electrodes (21, 22) onto the skin. Hence, electrode motion artifacts can be reduced and the signal quality over time is significantly improved.

When the electrodes (21, 22), the base (23a) of the main circuit (23) and the conductors (24) of the recorder (2) are based on one and the same flexible printed circuit board (FPCB) (5), the electrodes (21, 22) are dry electrodes and no interfaces are present in between. Hence, the recorder (2) does not break apart or experience connection problems, even under severe physical strain. Furthermore, cable motion artifacts are reduced. These characteristics result in a particular robust and easy wearable cuff (1). Additionally, the adaptivity of the cuff (1) to the skin of the living body is enhanced.

When the carrier material (4) is an elastic carrier material (4) having an elongation of at least 10%, in particular of at least 50%, at a tensile force of 1 N, when measured at 23° C. and 50% relative humidity, measured according to ISO 13934-1:2013, and when the conductors (24) exhibit a zig-zag, U-shape, Ω-shape and/or a meandering form, the cuff (1) allows to absorb motions of the skin of a living body, e.g. from muscle tension and relaxation, in particular for long-term ECG recording at an upper arm (3) of a human body. Hence, the zig-zag, U-shape, Ω-shape and/or a meandering form of the conductors (24) allow elongating as well as bending the conductors (24). This is of particular importance when the conductors (24) are directly arranged on the carrier material (4). Thus, the conductors (24) can follow all movements of the carrier material (4), even when the conductors (24) are based on rigid material which itself does not allow elongation or bending to the extent of the carrier material (4) alone. Thus, these characteristics result in a particular adaptive, easy wearable and robust cuff (1). Furthermore, connection problems between the electrodes (21, 22) and the skin are avoided to continuously maintain a high quality of the measured biosignals.

When the carrier material (4) is comprising a woven and/or a nonwoven layer (41) coated with a thermoplastic polymer layer (42), wherein the thermoplastic polymer layer (42) preferably comprises polyurethane (PU), the recorder (2)—in particular the base (23a) of the main circuit (23) and the conductors (24) of the recorder (2)—can easily be affixed to the carrier material (4), e.g. by lamination using heat and/or pressure to provide a strong and long-lasting connection between the recorder (2) and the carrier material (4). As such, detachment of the recorder (2) from the material (4) becomes essentially impossible under standard use conditions. These characteristics further enhance the robustness and easy wearability of the cuff (1). Additionally, the adaptivity of the cuff (1) to the skin of the living body is enhanced. Furthermore, these features allow a simple and straight-forward production of the cuff (1) with no extra production steps and an easy integration of the recorder (2) into the cuff (1).

Thus, the robust, adaptive and easy wearable cuff (1) with an integrated signal recorder (2) can be achieved with said independent features, wherein the combination of two or even all three features increase the robustness, the adaptivity and the easy wearability of the cuff (1) even more. And as such, the cuff (1) with the integrated signal recorder (2) is a stretchable and bendable cuff (1) in all dimensions. Hence, it is a flexible, 3-D stretchable and bendable cuff (1).

US-A-2017/0281038 describes a wearable device for continuously monitoring a condition of a subject, wherein the device is comprising a plurality of sensors and a processing circuitry coupled to the sensors. The plurality of sensors and the circuitry are formed in a polymer-based material comprising a plurality of openings through which the plurality of electrodes protrude from an inside of the polymer-based material to the outside of said material. The polymer-based material is configured to conform to a surface of the subject without causing signal degradation in the sensors and circuitry. Said polymer-based material may comprise parylene C, a poly(p-xylylene) polymer being used as moisture and dielectric barrier. However, a reversible compressible material is not disclosed, and it is also silent about a flexible printed circuit boards (FPCB), an elastic carrier material, and carrier material being coated with a thermoplastic polymer layer. It is noted that parylene polymers cannot form reversible compressible materials according to the invention.

US-A-2015/0313542 discloses a wearable article comprising a flexible band, one or more biosensors located in the flexible band, one or more processing units located in the flexible band, and at least one connecting mechanism configured to connect at least one end of the flexible band to a housing of a watch face. The sensing module may comprise silver chloride, thus wet sensing modules are disclosed. However, dry electrodes which are an integral part of a FPCB are not mentioned. It is also silent about conductors exhibiting a zig-zag, U-shape, Ω-shape and/or a meandering form. Furthermore, it does not disclose a carrier material being coated with a thermoplastic polymer layer and/or having a defined, minimal elongation. Additionally, it does not disclose flexible connections which allow widening e.g. of the upper arm. Thus, the disclosed article is not suitable for recording long-term ECG at an upper arm of a human body, e.g. it does not exhibit robust and adaptive properties.

WO-A-2010/088325 describes a device comprising a substrate and a plurality of electrodes mounted to the substrate and configured to sense an ECG signal of a patient when the plurality of electrodes is placed in contact with the patient. FPCB as a carrier material being coated with a thermoplastic polymer layer are not disclosed. It is also silent about conductors exhibiting a zig-zag, U-shape, Ω-shape and/or a meandering form.

The EP-A-3 292 885 discloses a stretchable electrode conductor arrangement for a medical implant having at least one zigzag or meandering conductor track on an insulation support with an insulation cover that is tightly connected with the support and embedding the conductor track. The support has an essentially non-stretchable material and being cut in a zigzag or meandering pattern to adapt it to the contour of the conductor track(s). The electrode conductor arrangement comprises multiple conductor tracks with vias to selected disc-shaped electrode poles. The conductor arrangement is designed to become part of a medical implant such as an electrically active catheter. Hence, it is proposed to be arranged around a stretchable PU- or silicone tube. However, the electrodes do not contain further components and a main circuit is not disclosed. Furthermore, a cuff comprising reversible compressible material as well as performing ECG-measurements are not mentioned.

And the EP-A-3 225 156 discloses an adaptive wearable device that measures physiological conditions, methods of operating the device, and computer programs for use with the device. It provides improved reliability in data due to the adaptive structure. Furthermore, an apparatus is provided that includes a support structure configured to at least partially enclose the torso or an appendage of a user, a spring module disposed on the support structure, as well as a first section of flexible circuitry and a first sensor, both disposed on the spring module. The sensor is configured to monitor the user and disposed onto the flexible circuitry. The sensor is embedded inside a polymer material. The device is designed to measure biosignals and vital signals, such as— among others—ECG. However, measuring said biosignals—and in particular ECG—is not disclosed sufficiently to be enabled by a skilled person in the art. Additionally, little is said about the support structure.

The Cuff (1)

The cuff (1) according to the invention is a robust, adaptive and easy wearable cuff (1) designed for measurements of biosignals on the skin, i.e. on the outer surface, of a living body, of a living body and/or for long-term measurements, i.e. up to 30 days. As such, the cuff (1) comprises an integrated signal recorder (2).

The term "robust cuff (1)" stands for a cuff having no connection problems, even after long-term wearing of the cuff (1), e.g. at an upper arm (3) of a human body, and after an unlimited number of muscle contractions and relaxations during the wearing of the cuff (1). Hence, the measurement of the biosignals is not interrupted at any time.

The term "adaptive cuff (1)" stands for a cuff which adapts—basically during the whole duration when wearing the cuff (1)—to the skin of a living body, also during contractions and relaxations of the muscles enclosed by the cuff (1). As such, the electrodes (21, 22) of the cuff (1) maintain the contact to the skin of the living body and good quality of the measured biosignals is provided constantly, independent on any motion of the muscles enclosed by the cuff (1).

The term "easy wearable cuff (1)" stands for a cuff which is easy to wear for the individual and as such wearing the cuff (1) is not a hassle. Hence, no regard for the cuff (1) is required during the individual's daily life, even when the muscles enclosed by the cuff (1) are contracted—e.g. during physical activity.

The term "biosignal"—is according to the invention— understood to stand for the time-varying bioelectrical signals which are measured and have diagnostic potential. Thus, the biosignals which can be measured with the cuff (1) may be biosignals from electrocardiography (ECG), electroencephalography (EEG), electromyography (EMG), or other biosignals from plethysmography, impedance and/or temperature measurements.

According to the invention, the term "living body" is understood to stand for a living human body as well as living animal bodies, in particular mammals, having a certain minimal size. The skilled person can easily evaluate the minimal size required of the human or animal.

In a particularly preferred embodiment, the cuff (1) is dedicated to record long-term ECG at an upper arm (3) of a human body.

In another preferred embodiment, the cuff (1) is not configured to connect by cables to a housing of a watch face. Furthermore, the cuff (1) is—among others due to its size— preferably not suited to wear it on a wrist. It is noted that biosignals, in particular ECG-signals, are weak at the level of the wrist.

The cuff (1) may be worn at an upper arm, at an upper leg or at the torso, i.e. upper body. It should be possible to place the cuff (1) sufficiently tight around the targeted place, e.g. around the upper arm or the torso, of the living body. As such, most preferably it is close-fitting to the skin. Thus, the cuff (1) may be an elastic, round cuff which can be placed e.g. around an arm. Alternatively—or in addition—the cuff (1) may comprise a fastener, e.g. a hook and loop fastener, a snap fastener, a clasp and/or a catch to adjust the cuff (1) to the required individual size.

The cuff (1) may be a cuff dedicated for measuring the biosignals only. Alternatively, the cuff (1) may be combined with another cuff, e.g. a cuff to measure the blood pressure, resulting in a multi-functional cuff to measure both, biosignals such as the ECG as well as blood pressure.

The cuff (1) according to the invention is based on a carrier material (4) and the signal recorder (2). The latter is comprising an optional ground electrode (21), one or more signal electrodes (22), a main circuit (23) comprising a base (23a), as well as conductors (24) which connect the electrodes (21, 22) to each other and/or to the base (23a) of the main circuit (23). The conductors (24), and thus most of the recorder (2), are most typically connected to the carrier material (4). Furthermore, at least one, preferably all, electrodes (21, 22) are connected to the carrier material (4) via the reversibly compressible material (6). The base (23a) of the main circuit (23) may be connected to the carrier material (4) and/or to an electrode (21, 22), e.g. to the ground electrode (21), if present.

In a particularly preferred embodiment, the electrodes (21, 22) of the cuff (1) are dry electrodes.

In another particularly preferred embodiment of the cuff (1), the electrodes (21, 22), the base (23a) of the main circuit (23) and the conductors (24) are based on one and the same flexible printed circuit board (FPCB) (5) and thus they exhibit no interfaces in between, and
- the carrier material (4) of the cuff (1) is an elastic carrier material (4) having an elongation of at least 10%, in particular of at least 50%, at a tensile force of 1 N, when measured at 23° C. and 50% relative humidity, measured according to ISO 13934-1-2013, and/or
- the carrier material (4) is comprising a woven and/or a nonwoven layer (41) being coated with a thermoplastic polymer layer (42), wherein the thermoplastic polymer layer (42) preferably comprises—in particular is based on—polyurethane (PU), wherein the electrodes (21, 22) are preferably dry electrodes.

The flexible printed circuit board (FPCB) (5)

According the present invention the electrodes (21, 22), the base (23a) of the main circuit (23) and/or the conductors (24) are based on a flexible printed circuit board (FPCB) (5).

In a particularly preferred embodiment, the electrodes (21, 22), the base (23a) of the main circuit (23) and the conductors (24) are based on one and the same flexible printed circuit board (FPCB) (5). Thus, they exhibit no interfaces in between and therefore they cannot break apart when used according to instructions. Thus, the recorder (2) does not break apart or experiences connection problems, even under severe physical strain.

In one preferred embodiment, the flexible printed circuit board FPCB (5) is a layered composite material comprising a first conductive material layer (51) as contact layer to the skin, in particular to the skin of the arm (3), a first dielectric layer (52), a signal layer (53), optionally an adhesive layer (54), a further dielectric layer (55), an optional further signal layer (56) and/or an optional solder mask layer (57), wherein the first conductive material layer (51) may be laser-machined and/or coated to provide a 3-D patter, and/or the side of the FPCB (5), which is opposite to the electrodes (21, 22), may be coated with an optional dielectric coating (58). These layers may be arranged in said order. However, they may be in any order, as long as the conductive layers (51, 53, 56) are separated from each other by a dielectric layer (52, 55). Furthermore, the FPCB (5) may comprise additional layers, e.g. further signal layers and dielectric layers. The skilled person is aware of the optimal FPCB for specific uses and he can make the selection. Additionally, he is also capable of manufacturing suitable FPCB's. The side of the FPCB (5), which is opposite to the electrodes (21, 22), may be coated with a dielectric coating (58). The optional dielectric coating (58) is preferably comprising of a Parylene-type material. Such Parylene-type materials such as Parylene C, Parylene D, Parylene HT or Parylene N, are inert, hydrophobic polymeric coating materials based on Poly-p-xylylene, and/or halogenated polymers thereof. A preferred coating comprises Parylene C or is a multi-component coating based on Parylene C, $SiO_2$ and ceramic. Parylene-type materials and coatings containing the same are known to the skilled person in the art.

Although the signal layer (56) may be covered with the optional solder mask layer (57), it well may be advantageous to further coat the components (5b-h) with an optional dielectric coating (58), such as coating comprising a Parylene-type material. It is noted that the layers (56, 57) and the coating (58) is arranged on side of the FPCB (5) which is opposite to the electrodes (21, 22).

The first conductive material layer (51) is present in the electrodes (21, 22), but most typically it is removed, e.g. etched away, for the main circuit (23) and the conductors (24). The layer (51) is connected by a vertical interconnected access (via) with the signal layer (53), which itself is connected to the main circuit (23). Hence, the layer (51) measures biosignals on the skin. They are then transported through the via to the signal layer (53), optionally amplified and/or filtered by the preamplifier or buffer (22a), and further transported to the main circuit (23) for processing.

In one embodiment, the first conductive material layer (51) is integrated into, i.e. it is, the signal layer (53). As such, a specific area of the layer (53), e.g. of the size of a typical layer (51), i.e. electrode, is not covered by the dielectric layer (52) to provide proper electrical contact to skin.

In another embodiment, the first conductive material layer (51) is integrated into, i.e. it is, the signal layer (53). As such, a specific area of the layer (53), e.g. of the size of a typical layer (51), i.e. electrode, is covered by the dielectric layer (52) and the signal layer (53) is therefore capacitively coupled to the skin.

The first conductive material layer (51) may be laser-machined and/or coated to provide a 3-D pattern for a better electrical contact to skin and thus to obtain even a better signal quality, e.g. an improved signal-to-noise ratio. Non-limiting, suitable materials to coat the layer (51) are electrically conductive materials and include silver (Ag), gold (Au), copper (Cu), electroless nickel immersion gold (ENIG), iridium-platinum (Ir—Pt), iridium dioxide ($IrO_2$), titanium nitride (TiN), and/or polymers such as poly-3,4-ethylendioxythiophen (PEDOT) and silver-polydimethylsiloxane (Ag-PDMS). The thickness of such a coating may be between 0.05 µm and 1 µm, measured with X-ray according to DIN ISO 3497 or—if unsuitable for the specific case—scanning electron microscopy (SEM). The skilled person can make the proper selection.

The conductive material layer (51) and the one or more signal layers (53, 56) may be of the same or of a different material. Suitable conductive materials for the layers (51, 53, 56) are known to the skilled person. Non-limiting, but preferred materials for the conductive layers (51, 53, 56) include Cu, Au, Ni, Cr, Pd, Al, Ag, Sn, Pt, Ir—Pt and/or electrically conductive polymers such as PEDOT or Ag-PDMS. The thickness of the layer (51) is preferably between 5 µm and 50 µm, in particular between 10 µm and 30 µm. The thickness of the layer (53) is preferably between 5 µm and 50 µm, in particular between 5 µm and 20 µm. And the thickness of the optional layer (56) is preferably between 5 µm and 50 µm, in particular between 10 µm and 40 µm, measured with X-ray according to DIN ISO 3497 or—if unsuitable for the specific case—scanning electron microscopy (SEM). The skilled person can make the proper selection.

The first and the further dielectric layers (52, 55) separate the conductive layers (51, 53, 56) from each other. Suitable dielectric materials for the layers (51, 53, 56) are known to the skilled person. Non-limiting, but preferred materials for the dielectric layers (52, 55) include liquid-crystal polymer (LCP) and/or polyimide (PI). LCP—as example—provides a number of advantageous properties, including biocompatibility, high mechanical flexibility and strength, good dielectric characteristics, multilayer circuit capabilities, high compatibility to the solder mask material, high durability, very low water absorption, excellent high-frequency electrical properties and thus it is suitable for RF applications and is chemically inert. Furthermore, LCP allows to cut out arbitrary forms from a sheet of FPCB, e.g. by laser cutting.

The thickness of the layer (52) is preferably between 10 µm and 200 µm, in particular between 25 µm and 100 µm, and the thickness of the layer (55) is preferably between 5 µm and 50 µm, in particular between 5 µm and 20 µm. And the thickness of the optional layer (56) is preferably between 10 µm and 100 µm, in particular between 15 µm and 50 µm, measured with X-ray according to DIN ISO 3497 or—if unsuitable for the specific case—scanning electron microscopy (SEM). The skilled person can make the proper selection.

The optional adhesive layer (54) adheres typically a conductive layer (51, 53, 56) to a dielectric layer (52, 55). Depending on the specifically used conductive layers (51, 53, 56) and dielectric layers (52, 55) and/or the process to manufacture the FPCB, the adhesive layer (54) might be omitted. Suitable adhesives for the layer (54) are commercially available and known to the skilled person in the art. A non-limiting, but preferred adhesive includes ULTRA-LAM®, in particular ULTRALAM® 3908. He also can make the best selection. A typical thickness of the layer (54) ranges preferably between 5 µm and 50 µm, in particular between 10 µm and 40 µm, measured with X-ray according to DIN ISO 3497 or—if unsuitable for the specific case—scanning electron microscopy (SEM). The skilled person can make the proper selection.

The optional solder mask layer (57) forms—when present—the final layer of the FPCB (5) and thus covers and protects the layer underneath. In case the latter is e.g. a dielectric layer (52, 55) with sufficient resistance to the environment, the layer (57) may be omitted. Suitable materials for the layer (57) are commercially available and known to the skilled person in the art. He also can make the best selection. A typical thickness of the layer (57) ranges preferably between 5 µm and 50 µm, in particular between 10 µm and 40 µm, measured with X-ray according to DIN ISO 3497 or—if unsuitable for the specific case—scanning electron microscopy (SEM). The skilled person can make the proper selection.

The Signal Recorder (2)

The signal recorder (2) is comprising an optional ground electrode (21), one or more signal electrodes (22), a main circuit (23) and conductors (24).

In a particular preferred embodiment, the one or more electrodes (21, 22) are dry electrodes. As such, no liquids are required and thus the major limitations of wet electrodes, such as deterioration or skin irritations when used on living skin over time, are eliminated. Thus, the dry electrodes (21, 22) are an integral part of the FPCB (5), i.e. the electrodes (21, 22) are made from one and the same FPCB (5), i.e. they typically are based on the first conductive material layer (51). Hence, the dry electrodes (21, 22) are made from the FPCB (5).

Furthermore, the electrodes (21, 22) and/or the section of the conductors (24) which is closest to the electrodes (21, 22), are preferably spiral shaped to add freedom of movement in the horizontal plane as well as in the vertical direction. This might reduce signal artifacts related to body motions, such as electrode motion relative to the skin. To increase contact pressure, the electrodes are equipped with the reversibly compressible material (6) placed between the textile and the solder mask layer (57) of the electrode (21, 22). The term "spiral shaped" is understood to include a single spiral, i.e. only one conductor (24) forms a spiral, as well as a double-, triple- or multi-spiral, i.e. a double-, triple or multi-helix, i.e. two, three or even more conductors (24) form together at least one spiral or helix. Thus, it may exhibit a helical form, wherein this term includes a multi-helix form.

The ground electrode (21) is optional, although in general recommended, since its presence improves the signal quality. However, if e.g. space for signal recording is too rare, e.g. when measuring the ECG at an upper arm of a premature baby, the ground electrode (21) may be omitted.

In one preferred embodiment, the signal recorder (2) comprises a ground electrode (21), wherein the main circuit (23) is affixed to the ground electrode (21), i.e. to the layer opposite the first conductive material layer (51), which will contact the skin, of the ground electrode (21).

The recorder (2) comprises at least one signal electrode (22). For improved data collection—and when space allows—it is helpful when the recorder (2) comprises two or more signal electrodes (22).

In one preferred embodiment, the FPCB (5) is a layered composite material, and the electrodes (21, 22) are dry electrodes, wherein the first conductive material layer (51) constitutes the recording part of the electrodes (21, 22), i.e. the layer (51) records the biosignals from the skin and conducts them to the main circuit (23), the base (23a) of the main circuit (23) and the conductors (24) most typically do not contain the first conductive material layer (51) of the FPCB (5). However, the base (23a) and the conductors (24) are comprising, and particularly consist of, the first dielectric layer (52), the signal layer (53), the adhesive layer (54), the further dielectric layer (55), and the optional signal layer (56) and/or the solder mask layer (57), and/or the conductors (24) exhibit a zig-zag, U-shape, Ω-shape and/or a meandering form.

Non-limiting examples of a suitable preamplifier or a buffer (22a) include dedicated inverting or non-inverting operational amplifier (opamp) circuits or in the case of the buffer, voltage follower circuits built using opamps or metal oxide semiconductor field effect transistor (MOSFET) circuits.

In a preferred embodiment, the main circuit (23) of the cuff (1) according to the present invention comprises besides the base (23a) an amplifier (23b), a controller (23c), optionally a battery (23d). Furthermore, the main circuit (23) may comprise as optional components a memory (23e), a transmitter or transceiver (23f), a DC-restorer (23g) and/or a feedback circuit (23h), although at least either a memory (23e) or a transmitter or transceiver (23f) is part of the main circuit (23). Alternatively—or in addition—the one or more signal electrode (22) comprise a preamplifier or a buffer (22a), thus to become a so-called active electrode. Hence, the recorded signals from the first conductive material layer (51) are preamplified—preferably as close as possible to the measurement point. This leads to lower susceptibility to magnetic or electrical field coupling and thus to a finally higher signal quality. The transmitter or transceiver (23f) can be powered by the battery (23d) of the main circuit (23), or the transmitter or transceiver (23f) can be powered by an external power source, thus making the battery (23d) of the circuit (23) redundant. Alternatively, or in addition, the transmitter or transceiver (23f) may be used to recharge the battery (23d) of the main circuit (23). In this case, the transmitter or transceiver (23f) most typically comprise a coil.

In another preferred embodiment, the amplifier (23b), the controller (23c), the optional battery (23d), the optional memory (23e), the optional transmitter or transceiver (23f), the optional DC-restorer (23g) and/or the optional feedback circuit (23h) of the main circuit (23) are connected to at least one of the signal layers (53, 56) of the base (23a), wherein the side of the FPCB (5), which is opposite to the electrodes (21, 22), may be coated with the optional dielectric coating (58). The components (23b-h) are commercially available components and known to the skilled person in the art. He is well capable of making the best selection. Furthermore, he knows how to properly assemble and connect them to at least one of the signal layers (53, 56) to result in a main circuit (23) with optimized performance.

The amplifier (23b) amplifies the recorded, analog signal for proper signal processing. A non-limiting example of a suitable amplifier (23b) is a battery-powered single-supply instrumentation amplifier with a gain of about 20 dB, a 3 dB bandwidth of 0.5 Hz-250 Hz and a CMRR of about 100 dB.

The controller (23c) converts the amplified analog biosignal to a digital signal, provides optional filtering and stores that signal in the memory (23e) and/or transmits it via the transmitter or transceiver (23f) to an external receiver. A non-limiting example of a suitable controller (23c) includes a 16-bit CPU, inputs and outputs, 128 KB non-volatile memory, 8 KB RAM and a 12-bit analog-to-digital converter with 10 channels, using a system clock of 12 MHz.

The battery (23d) provides the various components of the main circuit (23) sufficient electric energy. A non-limiting example of a suitable battery (23d) includes a lithium-ion battery with 4.2 V nominal voltage, having a capacity of 2000 mAh.

The memory (23e) stores the acquired and/or processed data. A non-limiting example of a suitable memory (23e) includes a non-volatile NAND flash, having a capacity of e.g. 8 GB.

The transmitter or transceiver (23f) transmits, i.e. reads out, the acquired and/or processed data on demand, based on a predefined interval and/or permanently by a wireless connection to an external computer, smartphone, smartwatch or another suitable receiver.

The transmitter or transceiver (5f) may comprise a coil enabling wireless power transmission, i.e. wireless power transfer (WPT), wireless energy transmission (WET) or electromagnetic power transfer, most typically making use of an electromagnetic field. Thus, the battery (5d) of the main circuit (5) may be recharged via the transmitter or transceiver (5f). A non-limiting example of a suitable transmitter or transceiver (23f) includes a compatible interface to the controller (23c), a Bluetooth® Low Energy or wireless module using another low-power network technology, RFID such as NFC, and/or optical wireless communication such as NIR, and an antenna.

The DC-restorer (23g) removes the offset from the amplified biosignal, introduced by electrode and/or conductor offset potentials, and therefore keeps the output signal in the required common mode range of the amplifier (23b). A non-limiting example of a suitable DC-restorer (23g) includes an inverting integrator opamp circuit.

The feedback circuit (23h) forces the body potential to a favorable circuit potential, e.g. the mid-supply voltage as well as actively suppresses the common mode voltage by negative feedback on the body, and hence at the input of the amplifier. A non-limiting example of a suitable feedback circuit (23h) includes an inverting low-pass filter opamp circuit.

The conductors (24) connect the electrodes (21, 22) to each other and/or to the base (23a) of the main circuit (23) and conduct the biosignal recorded with the electrodes (21, 22), i.e. with the first conductive material layer (51), to the main circuit (23).

The conductors (24) exhibit preferably a zig-zag, U-shape, Ω-shape and/or a meandering form. Thus, the conductors (24)—and therefore the signal recorder (2)—can also be stretched. This allows the recorder (2), when affixed the carrier material (4), to be stretched as the carrier material (4) is getting stretched.

The Carrier Material (4)

The cuff (1) according to the invention is formed using a carrier material (4) as base, into which the signal recorder (2) is integrated.

The carrier material (4) may comprise one single layer or of two or more layers. The carrier material (4) may also be—or comprise—e.g. a commercially available cuff to measure blood pressure.

In a particularly preferred embodiment of the present invention, the carrier material (4) is an elastic carrier material (4) having an elongation of at least 10%, in particular of at least 50%, at a tensile force of 1 N, when measured at 23° C. and 50% relative humidity, measured according to ISO 13934-1-2013. Thus, the conductors (24) exhibit preferably a zig-zag, U-shape, Ω-shape and/or a meandering form.

In another particularly preferred embodiment of the present invention, the carrier material (4) is comprising a woven and/or a nonwoven layer (41) being coated with a thermoplastic polymer layer (42). The thermoplastic polymer layer (42) allows an easy and straight-forward fixation of the base (23a) of the main circuit (23) and the conductors (24) based on FPCB (5) onto the carrier (4), e.g. by lamination using heat and/or pressure. Suitable thermoplastic polymers for the layer (42) are commercially available and known to the skilled person in the art. A particular preferred thermoplastic polymer comprises—in particular is based on—polyurethane (PU). The thickness of the layer (42) is preferably between about 5 μm and 75 μm, in particular between about 10 μm and 60 μm, measured with an optical micrometer.

In yet another particularly preferred embodiment of the present invention, the carrier material (4) is an elastic carrier material (4) i) having an elongation of at least 10%, in particular of at least 50%, at a tensile force of 1 N, when measured at 23° C. and 50% relative humidity, measured according to ISO 13934-1:2013. Thus, the conductors (24) exhibit preferably a zig-zag, U-shape, Ω-shape and/or a meandering form, and ii) is comprising a woven and/or a nonwoven layer (41) being coated with a thermoplastic polymer layer (42), wherein the thermoplastic polymer layer (42) preferably comprises—and in particular is based on—polyurethane (PU). The thickness of the layer (42) is preferably between about 5 µm and 75 µm, in particular between about 10 µm and 60 µm, measured with an optical micrometer.

In another preferred embodiment, the base (23a) of the main circuit (23) and the conductors (24) are mounted onto the carrier material (4), wherein the carrier material (4) is preferably:
coated with a thermoplastic polymer layer (42), in particular a polyurethane layer, wherein the base (23a) of the main circuit and the conductors (24) are mounted to the carrier material (4) by laminating—using most typically heat and/or pressure—the further dielectric layer (55) or the solder mask layer (57) of the base (23a) and the conductors (24) to the thermoplastic polymer layer (42) of the carrier material (4), and/or
a. By Sewing and/or Gluing the Conductors (24) to the Carrier Material (4).

Suitable carrier materials (4)—in particular of the woven and/or a nonwoven layer (41)—may be based on natural and/or chemical fibers, including textiles and fleeces. Preferred, non-limiting examples of suitable carrier materials (4) include materials based on polyurethanes and polyurethane block polymers, e.g. a block polymer based on polyurethane and polyether such as polyethylene glycol. Such carrier materials (4) are commercially available under the tradenames Elastane, Spandex, Dorlastan, Lycra, Creora, Elaspan, Acepora, Creora, INVIYA, ROICA, ESPA and Linel. The skilled person in the art is capable to make the best selection and he is aware of other suitable carrier materials (4).

The Reversibly Compressible Material (6)

According to the present invention, at least one—preferably all—electrodes (21, 22) are connected to the carrier material (4) via a reversibly compressible material (6).

In one preferred embodiment, the reversibly compressible material (6) acts as compressible spacer between the skin and the carrier material (4) of the cuff (1). Thus, the electrodes (21, 22) are connected to the carrier material (4) via the reversibly compressible material (6) as well as via the connectors (24) connecting the electrodes (21, 22) to the main circuit (23).

In another preferred embodiment, the reversibly compressible material (6) may be attached to—or being part of—the connectors (24), e.g. in the form of spring steel, e.g. in spiral form. As such, no additional spacing material is required, although still possible. Thus, the electrodes (21, 22) are connected to the carrier material (4) via the connectors (24) only. The latter connect the electrodes (21, 22) to the main circuit (23), wherein the connectors (24) comprise an integrated reversibly compressible material (6) such as e.g. a spring steel.

Hence, the connectors (24) comprise the reversible compressible material (6). Thus, the latter cannot be a Parylene-type polymer, in particular not Parylene-C, since this polymer has distinct different material properties.

Placing the reversibly compressible material (6) as a spacer between the carrier materials (4) and the electrode (21, 22)—or are the electrodes (21, 22) connected to the carrier material (4) via the connectors (24) only, wherein the connectors (24) comprise an integrated reversibly compressible material (6)—improves the contact to skin of the electrode (21, 22), even when the skin surface is changing, e.g. when muscles are contracted and relaxed. Hence, the quality of the recorded biosignals is clearly improved.

In a preferred embodiment, the reversibly compressible material (6) is affixed to the further dielectric layer (55), the signal layer (56) or the solder mask layer (57) of the electrodes (21, 22). Alternatively—or in addition—the reverse side of the compressible material (6), i.e. the side of the compressible material (6) which is opposite to the electrode (21, 22), is affixed to the carrier material (4). Hence, the compressible material (6) may be adhered to the carrier material (4), e.g. by gluing, welding and/or mechanically sticking.

In another preferred embodiment, the reversibly compressible material (6)
is comprising a spring, an elastomer and/or is based on one or more layers of the FPCB (5) in helical form, wherein the spring is preferably based on spring steel and the elastomer is preferably a foamed elastomeric polymer, and/or
can be compressed reversibly by at least 25%, in particular at least 50%, when a force of 1 N is applied, measured at 23° C. and 50% relative humidity, measured according to DIN EN ISO 3386-1 (2015-10).

The spring of the reversibly compressible material (6) may be a ledge spring, i.e. a spring using a ledge, a dome spring, a spiral spring and/or a foam spring, as disclosed in EP-A-3 225 156. Furthermore, the spring may be based on an elastomer and/or is based on one or more layers of the FPCB (5) in helical form, e.g. reinforced with spring steel. Preferably, the spring is based on a spring steel only or combined with an elastomer in the form of a foamed elastomeric polymer, since they allow not only reversible compression, but also movement in a direction which is e.g. parallel to the skin, without losing contact to skin. Preferred foamed elastomeric polymers are known to the skilled person in the art and include polyurethane foams, elastomeric polyether foams as well as styrene-butadiene rubber (SBR) foams. It is noted, however, that the reversibly compressible material (6) is not a Parylene-type polymer, in particular not Parylene-C, since this polymer has distinct different material properties, e.g. it is not a foamable elastomeric polymer.

In yet another preferred embodiment, the reversibly compressible material (6) can be compressed reversibly by at least 10%, preferably by at least 25%, in particular at least 50%, when a force of 1 N is applied, measured at 23° C. and 50% relative humidity, measured according to DIN EN ISO 3386-1 (2015-10).

The reversibly compressible material (6)—when intended for measurements of biosignals at the upper arm of a human—exhibits typically a height, i.e. the distance between the carrier material (4) and the electrode (21, 22), of about 0.5 cm to 5 cm, in particular of about 0.7 cm to 3 cm, in the uncompressed and, thus relaxed state.

Process to Make the Cuff (1)

The process to make the cuff (1) according to the invention comprises the steps of making the signal recorder (2) and mounting it to the carrier material (4).

In a first step, the one or more signal electrodes (22), the base (23a) of the main circuit (23), the conductors (24) and the optional ground electrode (21) of the signal recorder (2) are made from the same flexible printed circuit board (FPCB) (5). Thus, the FPCB (5) with the required architecture and comprising the wanted layers, e.g. the layers (51) to (57), is made and cut out, e.g. by laser cutting. The processes of making such suitable FPCB's and cutting out the desired form, in particular in a zig-zag, U-shape, Q-shape and/or a meandering form, are known to the skilled person in the art.

In another step, the amplifier (23b), the controller (23c), the battery (23d) and the optional memory (23e), the optional transmitter or transceiver (23f), the optional DC-restorer (23g) and/or the optional feedback circuit (23h) are connected to the base (23*a*) and thus to the main circuit (23), preferably by soldering, welding, bonding, and/or gluing. Furthermore, in case the one or more signal electrodes (22) contain a preamplifier or a buffer (22*a*), the preamplifier or buffer (22*a*) is connected to the signal electrode (22). The processes of making these connections are known to the skilled person in the art.

These two steps provide the signal recorder (2) and may be made in any order.

In yet another step, the signal recorder (2), i.e. the conductors (24) and the base (23*a*) of the main circuit (23), are mounted, i.e. affixed, e.g. glued, welded, mechanically stuck and/or adhered, to the carrier material (4). Preferably, and when the carrier material (4) comprises a thermoplastic polymer layer (42), the signal recorder (2) is laminated—using heat and/or pressure—to the carrier material (4), i.e. to the layer (42).

In even another step, the reversibly compressible material (6) is affixed, i.e. e.g. glued, welded, mechanically stuck and/or adhered, to at least one electrode (21, 22) and/or to the carrier material (4), wherein the compressible material (6) connects the electrode (21, 22) to the carrier material (4).

Furthermore, and in any order of the process according to the invention, the first conductive material layer (51) may be laser-machined and/or coated to provide a 3-D pattern, and/or the side of the FBCB (5), which is opposite to the electrodes (21, 22), may be coated with the optional dielectric coating (58).

Hence, the components (23*b-h*) are preferably arranged at the side of the FPCB (5) which is opposite to the electrodes (21, 22). And, upon coating said side with the dielectric coating (58), also the components (23*b-h*) are coated therewith. Applying the dielectric coating (58) onto the components (23*b-h*), and on e.g. the layer (56) or (57), may be carried out before and/or after cutting the FPCB (5).

Process to Measure Biosignals

The process according the invention to measure biosignals on the skin of a living body, in particular for long-term ECG recording at an upper arm (3) of a human body, with the cuff (1) according to the invention, comprises placing the cuff (1) with the integrated signal recorder (2) at a living body, in particular at the upper arm (3) of a human body. Afterwards, the body may be forced to a desired circuit potential, e.g. the mid-supply voltage and the common mode voltage is actively suppressed by negative feedback of the optional feedback circuit (23*h*). Simultaneously, the biosignals are measured, preferably continuously, with the electrodes (21, 22), optionally amplified and/or filtered by the preamplifier or buffer (22*a*), and transmitted via the conductors (24) to the main circuit (23) of the signal recorder (2). Furthermore, the biosignals may be amplified by the amplifier (23*b*), optionally clamped and/or filtered by the optional DC-restorer (23*g*), processed by the controller (23*c*), saved in the memory (23*e*) and/or transmitted to an external recorder via the transmitter or transceiver (23*f*).

The process to measure biosignals with the cuff (1) according to the invention may further comprise that:

the biosignals are measured, preferably continuously, with the signal electrodes (22), the thus obtained data be stored on the main circuit (23), in particular in the optional memory (23*e*) of the main circuit (5), wherein preferably all measured data are stored until the data are read out, and the measured and stored data are read out via the transmitter or transceiver (23*f*) using a wired or wireless communication such as Bluetooth Low Energy, RFID such as NFC or other low power communication technologies. However, when the main circuit (23) does not comprise a memory (23*e*), the data are read out continuously.

In a preferred embodiment of said process as well as of the cuff (1) according to the invention, and when the signal recorder (2) is placed onto the skin of a living body, the electrodes (21, 22)—in particular the first conductive layer (51) of the FPCB (5)

have direct contact to the skin, in particular to the skin of the upper arm (3) of a human body. With other words: there is no polymer layer or polymer casing between the electrode (21, 22), in particular the layer (51) which records the biosignals, and the skin. Thus, the recorded signals are not distorted and/or weakened by a—typically dielectric-layer between the skin and the layer (51), and/or the biosignals are amplified by the amplifier (23*b*), optionally clamped and/or filtered by the DC-restorer (23*g*), processed by the controller (23*c*), saved in the memory (23*e*) and/or transmitted to an external recorder via the transmitter or transceiver (23*f*).

In even another embodiment of the process to measure biosignals with the cuff (1) on the skin of a living body, the biosignals are measured with a cuff (1) comprising one signal electrode (22) and the ground electrode (21) and another cuff comprising a second signal electrode (22). The other cuff with a second signal electrode (22) may be a cuff (1) according to the invention or may be another cuff. Preferably, the cuff (1) is placed at one upper arm and the other cuff is placed at the other upper arm. In addition, the common mode voltage of the upper arm (3) of the human body is preferably reduced by the optional feedback circuit (23*h*).

In another embodiment, the process to measure biosignals according to the invention further comprises that the read out data are deleted from the memory (5*e*) of the monitor (1) and/or that the battery (5*d*) of the monitor (1) is recharged, preferably by Bluetooth Low Energy, RFID such NFC or other low power communication technologies. Recharging the battery (5*d*) of the main circuit (5) occurs preferably by wireless power transmission via the transmitter or transceiver (5*f*) wherein the transmitter or transceiver (5*f*) most typically comprise a coil.

The Use

The cuff (1) according to the invention and made according to the invention is particularly suited to record biosignals on the skin of a living body.

The living body is most typically a human or an animal, wherein the animal is preferably a mammal such as a monkey, dog, cat, horse, cow, donkey. Particularly preferred are humans, i.e. the human body. Alternatively, or in addition, the recording of the biosignal is preferably used for the measurement of biosignals such as electrocardiography (ECG), in particular long-term ECG, electroencephalography (EEG), electromyography (EMG), or biosignals from plethysmography, impedance and/or temperature measurements during short and/or long term.

In a particular preferred embodiment, the recording of biosignals on the skin of a living body is the long-term measurement of ECG at an upper arm (3) of a human body.

LIST OF CITED REFERENCE SIGNS

1 Cuff (1)
2 Signal recorder (2)
21 ground electrode (21)
22 one or more signal electrodes (22)

22a preamplifier or buffer (22a)
23 main circuit (23)
23a base (23a)
23b amplifier (23b)
23c controller (23c)
23d battery (23d)
23e memory (23e)
23f transmitter or transceiver (23f)
23g DC-restorer (23g)
23h feedback circuit (23h)
24 conductors (24)
3 Arm (3) of a human body
4 Carrier material (4)
41 woven and/or a nonwoven layer (41)
42 thermoplastic polymer layer (42)
5 Flexible printed circuit board (FPCB) (5)
51 first conductive material layer (51)
52 first dielectric layer (52)
53 further conductive material signal layer (53)
54 adhesive layer (54)
55 further dielectric layer (55)
56 further optional signal layer (56)
57 solder mask layer (57)
58 dielectric coating (58)
6 Reversibly compressible material (6)

Figure 1:
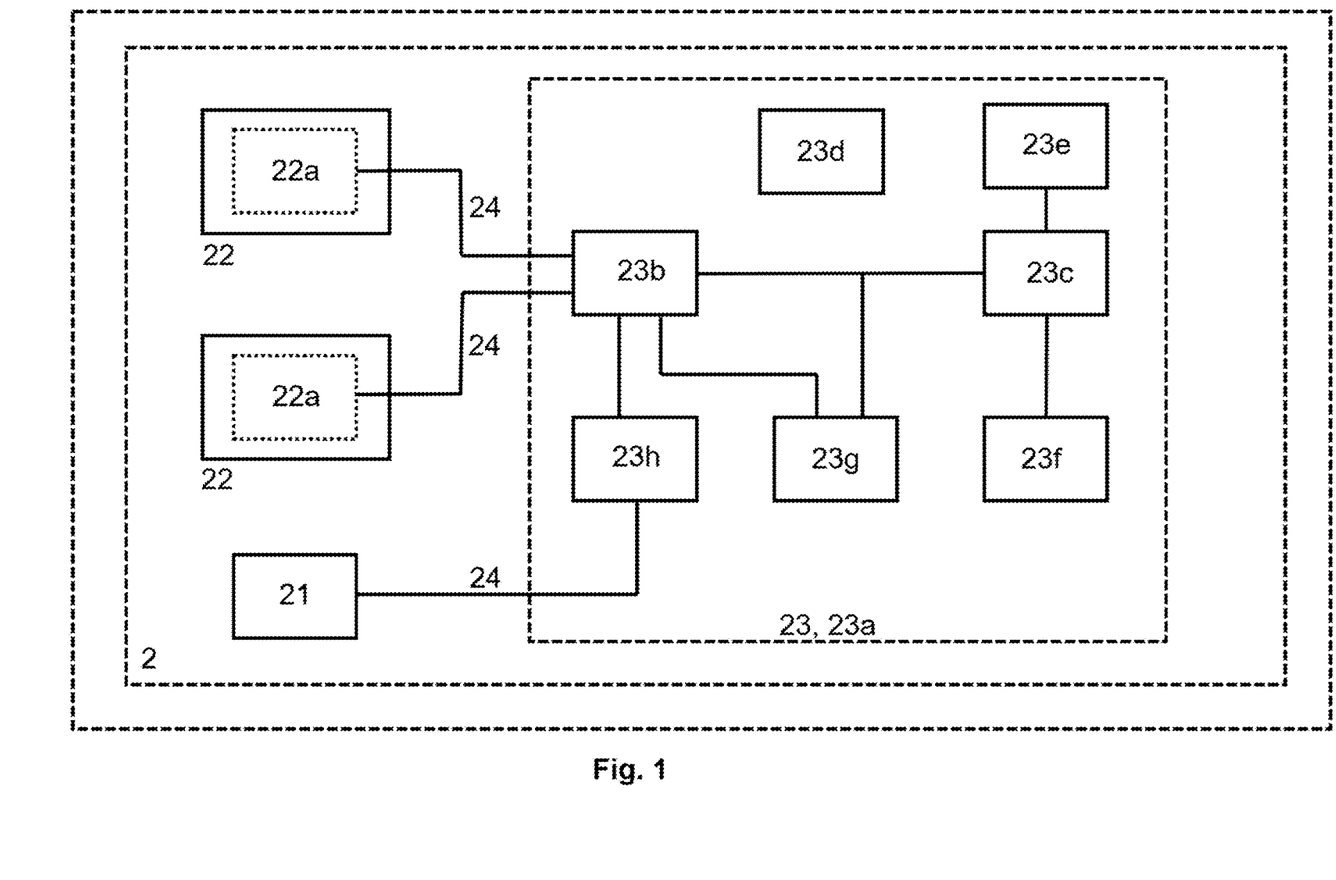
FIG. 1 shows a non-limiting block diagram of the cuff (1) with the signal recorder (2) according to the present invention.

The following figures present non-limiting embodiments, which are not restricting or narrowing the invention. These explanations are part of the description:

FIG. 1 discloses a non-limiting block diagram of the cuff (1) with the signal recorder (2). The latter comprises the ground electrode (21), two signal electrodes (22), each having a preamplifier (22a) integrated and the main circuit (23) with the base (23a), amplifier (23b), controller (23c), battery (23d), memory (23e), transmitter or transceiver (23f), DC-restorer (23g) and feedback circuit (23h). The conductors (24) connect the ground electrode (21) and the signal electrodes (22), respectively, to the main circuit (23). The battery (23d) is connected (not shown) to each component (21, 22, 22a, 23, 23a-h) to provide them with the required electricity.

Figure 2:
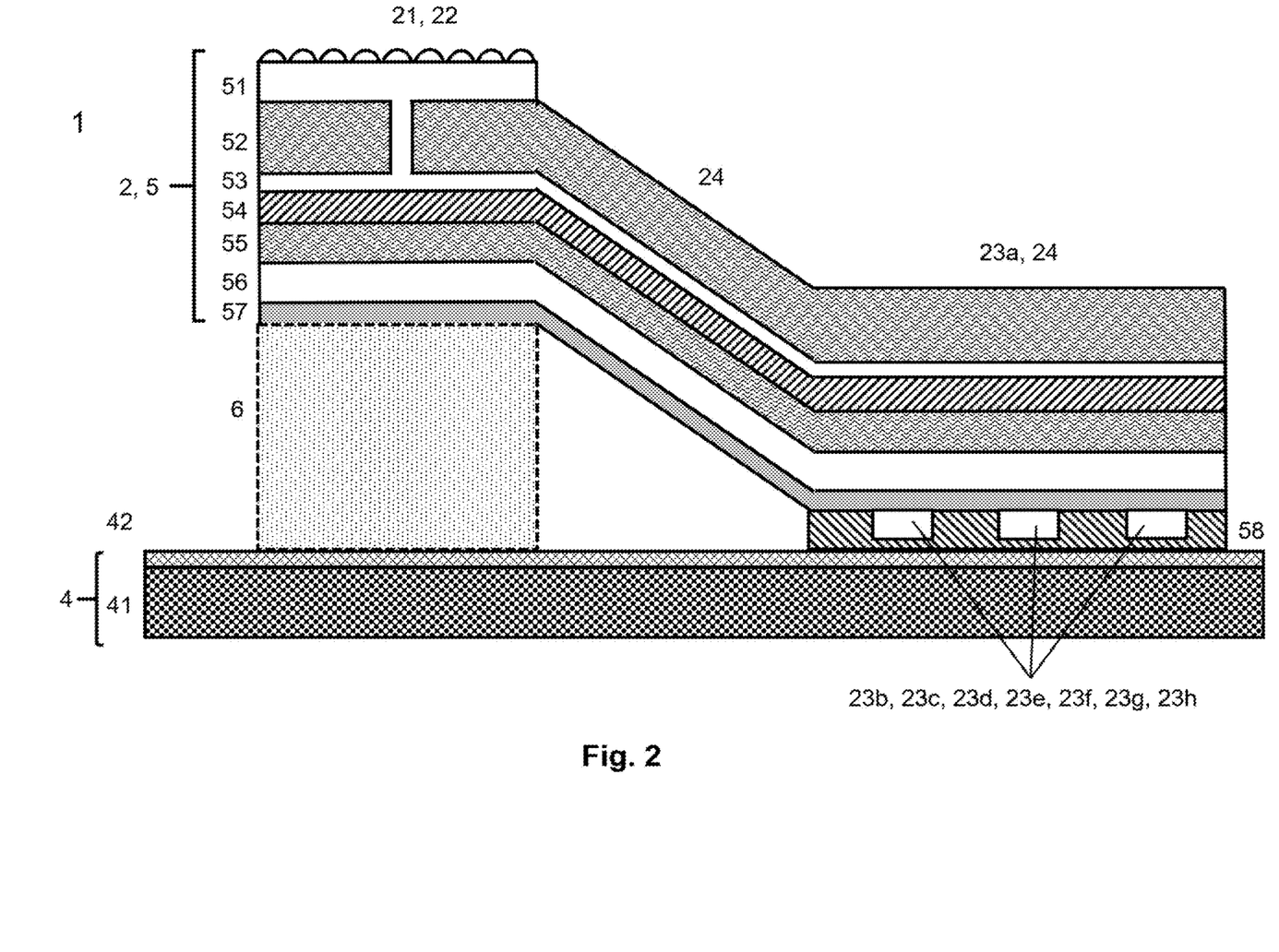
FIG. 2 shows an exemplary cross section of the cuff (1) comprising the carrier material (4) with the woven and/or a nonwoven layer (41) and the optional although preferred thermoplastic polymer layer (42)

FIG. 2 shows an exemplary cross section of the cuff (1) comprising the carrier material (4) with the woven and/or a nonwoven layer (41) and the optional—although preferred—thermoplastic polymer layer (42). The signal recorder (2) comprising an electrode (21, 22), the main circuit (23) with the base (23a) and the connector (24) is arranged on the carrier material (4). All said components (21, 22, 23a and 24) are made from the one and same material, i.e. FPCB (5). The base (23a) of the main circuit (23) and the conductors (24) compose in this example of the first dielectric layer (52), the further conductive material signal layer (53), the adhesive layer (54), the further dielectric layer (55), the further optional signal layer (56) as well as of the solder mask layer (57). The latter is laminated using heat and/or pressure to the thermoplastic polymer layer (42) of the carrier material (4).

On the left-hand side of the recorder (2) and the FPCB (5) are the various layers of an exemplary electrode (21, 22) visualized. The electrode (21, 22) comprises—in addition to the same FPCB-layers (52-57) from the base (23a) and the conductors (24)—the first conductive material layer (51), which is coated with a 3-D pattern for better contact to skin. The layer (51) is connected by a vertical interconnected access (via) to the further conductive material signal layer (53). Hence, the recorded biosignal is conducted from the layer (51) to the layer (53) of the electrodes (21, 22) along the layer (53) of the conductors (24) to the base (23a) of the main circuit (23), where it is further processed.

In case a preamplifier (22a) is attached to the signal electrode (22) (not shown in this figure), the preamplifier (22a) preferably is located opposite to the first conductive material layer (51), e.g. mounted onto the further optional signal layer (56).

Between the electrodes (21, 22) and the carrier material (4) is the reversible compressible material (6) arranged, allowing constant contact of the first conductive material layer (51) to the skin, even when the carrier material (4), e.g. with the arm (3), is changing its location.

The amplifier (23b), controller (23c), the optional battery (23d), the memory (23e), a transmitter or transceiver (23f)—which may comprise a coil, and the optional DC-restorer (23g), and/or feedback circuit (23h), are—indicated as a number of rectangles—exemplary arranged at the optional further signal layer (56). Furthermore, these components (23b-h) as well as the layer (56) in-between—are coated with the optional dielectric coating (58).

Figure 3:
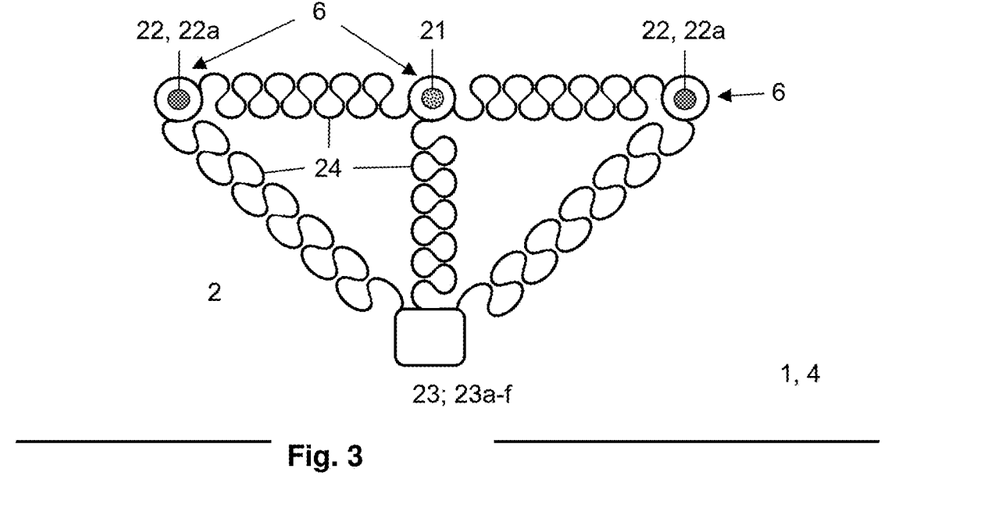
FIG. 3 shows a view from above onto the cuff (1) with the carrier material (4), onto which the signal recorder (2) is mounted.

FIG. 3 shows a view from above onto the cuff (1) with the carrier material (4), onto which the signal recorder (2) is mounted. The indicated recorder (2) comprises the ground electrode (21), which is arranged in-between the two lead electrodes (22) with integrated preamplifier (22a), the main circuit (23) and the conductors (24). The latter connect the electrodes (21, 22) with the main circuit (23). The represented conductors (24) have 0-shape, which provides the recorder (2) an increased flexibility, in particular also an elasticity basically in any direction. Hence, the recorder (2), when affixed to the carrier material (4), may exhibit a similar elasticity as the carrier material (4) and thus it does not disintegrate upon traction.

Between the carrier material (4) and the electrodes (21, 22) are reversible compressible materials (6) arranged, which are indicated, but not visible.

The main circuit (23) is arranged in a distance from all electrodes (21, 22), thus giving the recorder (2) a triangle form. However, it is also possible that the main circuit (23) is placed between the ground electrode (21) and the compressible material (6). Thus, a recorder (2) with three electrodes (21, 22) may only comprise two conductors (24). This arrangement is simpler and requires less space.

Figure 4:
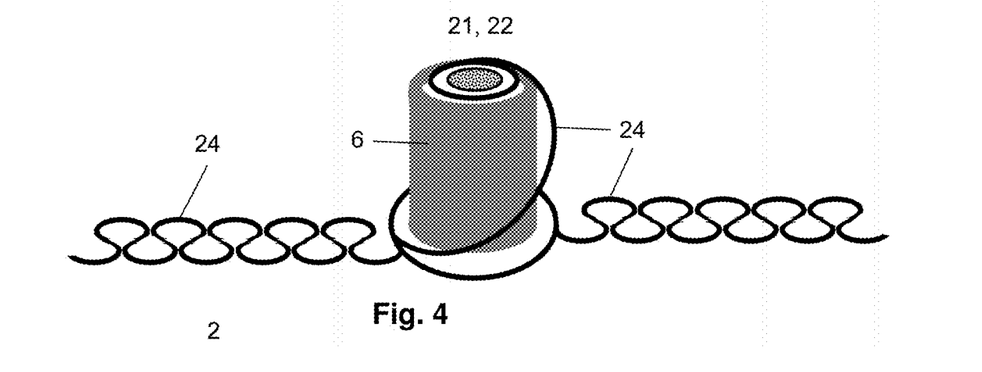
FIG. 4 shows an exemplified, expanded view of one electrode (21, 22) of the recorder (2) with conductors (24) and the reversibly compressible material (6)

FIG. 4 shows an exemplified, expanded view of one electrode (21, 22) of the recorder (2) with conductors (24) and the reversibly compressible material (6). In the area of the compressible material (6), the conductor (24) exhibits a type of spiral shape before it is converted into the electrode (21, 22) on top of the compressible material (6). This allows the electrode (21, 22) to be compressed together with the material (6) without being damaged.

Figure 5A:
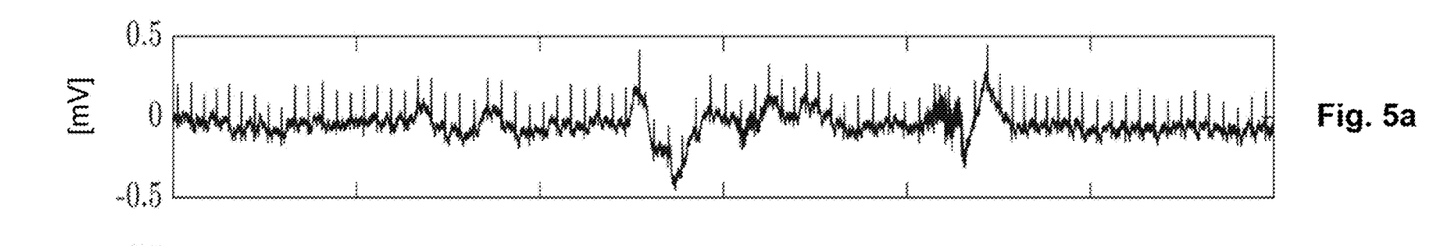
FIG. 5a shows unfiltered ECG signals recorded with a cuff (1) without reversibly compressible material (6) according to the invention.
Figure 5B:
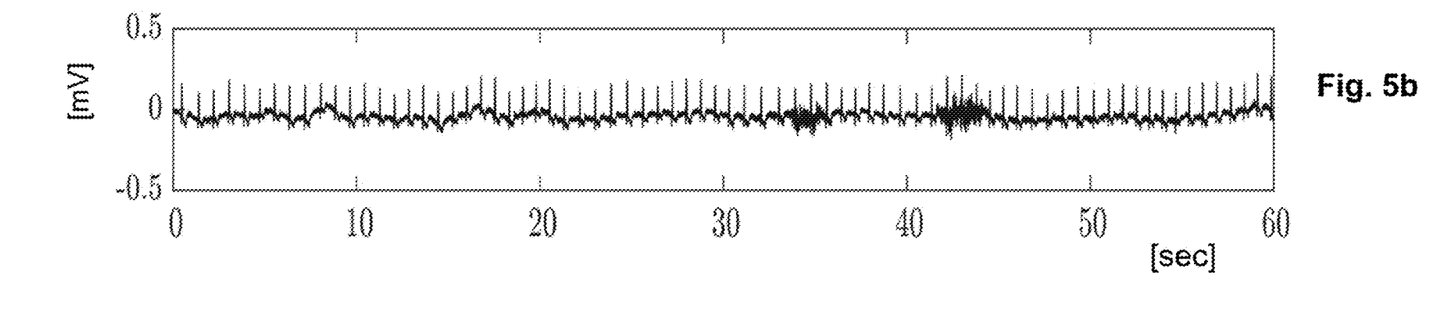
FIG. 5b shows unfiltered ECG signals recorded with a cuff (1) with reversibly compressible material (6) according to the invention.

FIG. 5 shows unfiltered ECG signals recorded with a cuff (1) with reversibly compressible material (6), i.e. according to the invention (FIG. 5b), and without compressible material (6), i.e. as reference experiment (FIG. 5a). The cuff (1) is placed at the left upper arm (3) of the person, who is at rest and sitting on a chair. The left arm is positioned on the left leg.

The recorder (2), which is integrated into the cuff (1) and used for this experiment, comprising one ground electrode (21) and two signal electrodes (22). The electrodes (21, 22) have in both experiments (FIG. 5a and FIG. 5b) direct contact to skin, i.e. they are not covered with a polymer layer. Furthermore, the electrodes (21, 22), the base (23a; not shown) of the main circuit (23; not shown) and the conductors (24; not shown) are based on the same FPCB (5).

In FIG. 5a is an ECG signal amplitude depicted using electrodes without a reversibly compressible material (6), i.e. without spring force. Hence, FIG. 5a indicates a reference biosignal.

In FIG. 5b is an ECG signal amplitude depicted using electrodes with a reversibly compressible material (6), i.e. with spring force. Hence, FIG. 5b indicates recorded biosignals according to the invention.

In both experiments, i.e. in FIG. 5a and FIG. 5b, the person lifts the left arm with the cuff (1) from the leg between 30 and 40 seconds and back again between 40 and 50 seconds. In the recorded signals of FIG. 5a is the effect of lifting the arm clearly visible, due to the bad signal quality and baseline instability. However, in FIG. 5b the same effect is hardly visible due to the high signal-to-noise ratio.

The comparison of the ECG signals from FIG. 5a to FIG. 5b reveals that the baseline in FIG. 5b is more stable. This is attributed to the higher contact pressure, which stabilizes the contact of the electrode to skin.

Figure 6:
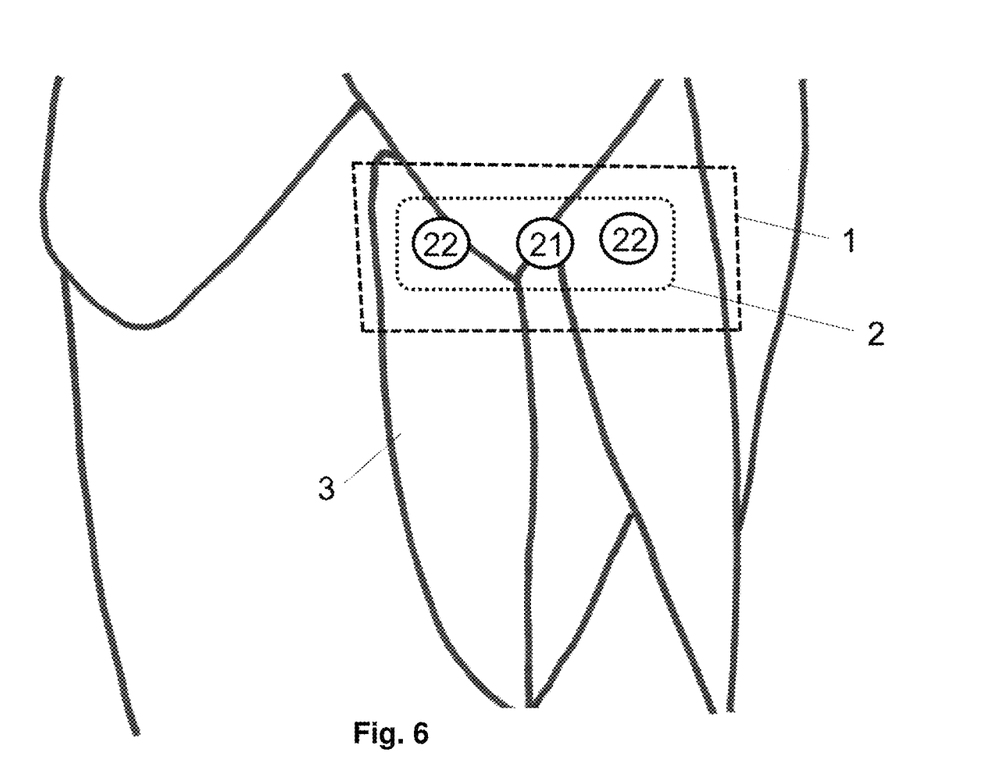
FIG. 6 indicates the muscles of the left upper arm (3) with a cuff (1) in front of the upper body of a human body.

FIG. 6 indicates the muscles of the left upper arm (3) with a cuff (1) in front of the upper body of a human body. The cuff (1) is outlined schematically with dashed lines—fixed around the upper arm (3). The cuff (1) comprises the recorder (2)—with dotted lines—with the ground electrode (21) with adjoining one signal electrode (22) on both sides, wherein the electrodes (21, 22) are located at the preferred position.

The ground electrode (21) is—in FIG. 6—located at the lower end of the deltoid muscle and between the biceps brachii muscle on the left and the triceps brachii muscle on the right side. Accordingly, the signal electrode (22) on the right side is located on the upper part of the triceps brachii muscle and the signal electrode (22) on the left side is located on the upper part of the biceps brachii muscle.

The invention claimed is:

1. A robust, adaptive, and easily wearable cuff with an integrated signal recorder configured to be fitted for measurements of biosignals on a skin of a living body, in particular for long-term ECG recording at an upper arm of a human body, wherein the cuff is based on a carrier material and the signal recorder is comprising:
    a first conductive material layer;
    at least one signal electrodes,
    a main circuit comprising a base, conductors which connect the at least one signal electrodes to each other and to the base of the main circuit, wherein at least one signal electrodes is connected to the carrier material via a reversibly compressible material, the reversibly compressible material is placed between the at least one signal electrodes and the carrier material;
    wherein the at least one signal electrodes, the base of the main circuit, and the conductors are made and cut out together from the same flexible printed circuit board (FPCB) and thus they exhibit no interfaces in between, wherein the biosignals are measured with the at least one signal electrodes, and transmitted within the one and the same signal recorder and thus without interfaces via the conductors to the main circuit of the signal recorder,
    wherein the carrier material is an elastic carrier material having an elongation of at least 10% at a tensile force of 1 N, when measured at 23° C. and 50% relative humidity, measured according to ISO 13934-1:2013, and
    wherein the conductors exhibit a zig-zag, a U-shape, a Q-shape, or a meandering form,
    wherein the reversibly compressible material:
        a) comprises a spring, an elastomer, or is based on one or more layers of the FPCB in helical form; and
        b) is compressed reversibly by at least 25%, when a force of 1 N is applied, measured at 23° C. and 50% relative humidity, measured according to DIN EN ISO 3386-1 (2015-10);
    wherein the reversibly compressible material allows a constant contact of the first conductive material layer to the skin, even when the carrier material changes location.

2. The cuff according to claim 1, wherein the main circuit further comprises an amplifier, a controller, a memory, a transmitter or transceiver, a DC-restorer, and a feedback circuit.

3. A process to make the cuff according to claim 2, wherein:
    the one or more signal electrodes, the base of the main circuit, and the conductors are made and cut out together from the same flexible printed circuit board (FPCB), wherein the biosignals are measured with the at least one signal electrodes, and transmitted the one and the same signal reorder, and thus, without interfaces via the conductors to the main circuit of the signal recorder,
    wherein the amplifier, the controller, and the memory, the transmitter or transceiver, the DC-restorer and the feedback circuit are connected to the base and thus to the main circuit, preferably by soldering, welding, bonding, or gluing,
    wherein the conductors and the base of the main circuit are mounted to the carrier material,
    wherein the reversibly compressible material is affixed to the at least one electrode or to the carrier material,
    wherein the compressible material connects the electrode to the carrier material.

4. The process according to claim 3, wherein
    a signal recorder of the cuff comprises a ground electrode, wherein the ground electrode is made from the same FPCB comprising the first conductive material layer,
    the main circuit further comprises a battery, wherein the battery is connected to the base and thus to the main circuit, preferably by soldering, welding, bonding, or gluing,
    the first conductive material layer is laser-machined or coated to provide a 3-D pattern; or
    the side of the FPCB, which is opposite to the electrodes, is coated with an optional dielectric coating.

5. The cuff according to claim 2, wherein the main circuit further comprises a battery connected to at least one of the signal layers of the base, or the at least one signal electrodes comprise a preamplifier or a buffer.

6. The cuff according to claim 1, wherein the FPCB is a layered composite material comprising a first conductive material layer configured to be fitted as contact layer to the skin, in particular to the skin of the upper arm, a first dielectric layer, and a signal layer.

7. The cuff according to claim 6, wherein:
    the at least one signal electrodes are dry electrodes, wherein the first conductive material layer constitutes the recording part of the at least one signal electrodes,
    the base of the main circuit and the conductors do not contain the first conductive material layer of the FPCB, and comprise the first dielectric layer, the signal layer, and a further dielectric layer.

8. The cuff according to claim 6, wherein the amplifier, the controller, the memory, the transmitter or transceiver, the DC-restorer, and the feedback circuit of the main circuit are connected to at least one of the signal layers of the base.

9. The cuff according to claim 6, wherein the signal recorder comprises a ground electrode, wherein the main circuit is affixed to the layer opposite the first conductive material layer of the ground electrode and the conductors connect the ground electrode to the one or more signal electrodes to each other and to the base of the main circuit, and wherein the ground electrode is connected to the carrier material via the reversibly compressible material.

10. The cuff according to claim 6, wherein:
a) the reversibly compressible material is affixed to the further dielectric layer, the signal layer, or the solder mask layer of the electrodes, or
b) the reverse side of the compressible material is affixed to the carrier material.

11. The cuff according to claim 6, wherein
the FPCB further comprises an adhesive layer, a further signal layer, or a solder mask layer; or
the first conductive material layer is laser-machined or coated to provide a 3-D pattern; or
the side of the FPCB, which is opposite to the electrodes, is coated with an optional dielectric coating.

12. The cuff according to claim 1, wherein the base of the main circuit and the conductors are mounted onto the carrier material, wherein the carrier material is:
coated with a thermoplastic polymer layer, in particular a polyurethane layer, wherein the base of the main circuit and the conductors are mounted to the carrier material, by laminating the further dielectric layer or the solder mask layer of the base and the conductors to the thermoplastic polymer layer of the carrier material, or
by sewing or gluing the conductors to the carrier material.

13. The cuff according to claim 1, wherein the reversibly compressible material:
a) comprises a spring, an elastomer or is based on one or more layers of the FPCB in helical form, wherein the spring is based on spring steel and the elastomer is a foamed elastomeric polymer, or
b) can be compressed reversibly by at least 50%, when a force of 1 N is applied, measured at 23° C. and 50% relative humidity, measured according to DIN EN ISO 3386-1 (2015-10).

14. A process configured to be fitted to measure biosignals on the skin of a living body for long-term ECG recording at the upper arm of a human body with the cuff according to claim 1, the process comprising the steps of:
the cuff with the integrated signal recorder is adapted to be placed on the upper arm of a human body,
continuously measuring the biosignals with the electrodes, and transmitted via the conductors to the main circuit of the signal recorder.

15. The process according to claim 14, wherein when the signal recorder is placed onto the skin of a living body,
the electrodes, in particular, the first conductive layer of the FPCB, have direct contact to the skin, in particular, of the skin of the upper arm of a human body, and/or
the biosignals are amplified by the amplifier, optionally clamped and/or filtered by the DC-restorer, processed by the controller, saved in the memory and/or transmitted to an external recorder via the transmitter or transceiver.

16. The process according to claim 14, wherein the process further comprises the steps of:
a common mode voltage is reduced with the feedback circuit, or
the biosignals are amplified, filtered, or buffered.

17. The process according to claim 15, wherein the biosignals are further clamped or filtered by the DC-restorer.

18. The cuff according to claim 1, wherein the carrier material comprises a woven or a nonwoven layer being coated with a thermoplastic polymer layer, wherein the thermoplastic polymer layer comprises polyurethane.

* * * * *